United States Patent [19]
Colella et al.

[11] 3,933,913
[45] Jan. 20, 1976

[54] N,N'-BIS[2-3-SUBSTITUTED-4-HYDROXYPHEYL)-2-HYDROXYETHYL)]-POLYMETHYLENEDIAMINES

[75] Inventors: Donald F. Colella, Philadelphia, Pa.; Carl Kaiser, Haddon Heights, N.J.

[73] Assignee: SmithKline Corporation, Philadelphia, Pa.

[22] Filed: Sept. 8, 1972

[21] Appl. No.: 287,399

Related U.S. Application Data

[63] Continuation-in-part of Ser. No. 148,912, June 1, 1971, abandoned.

[30] Foreign Application Priority Data

May 25, 1972  South Africa............... 72/3611

[52] U.S. Cl..... 260/570.6; 260/343.7; 260/453 AR; 260/471 A; 260/501.1; 260/501.12; 260/501.18; 260/501.19; 260/501.2; 260/553 A; 260/556 A; 260/556 N; 260/559 R; 260/559 D; 260/562 R; 260/570.5 C; 260/570.5 P; 260/570.8 R; 260/575; 260/592; 424/280; 424/316; 424/320; 424/321; 424/322; 424/330

[51] Int. Cl.²......................................... C07C 91/22

[58] Field of Search............ 260/570.6, 570.5, 501.1

[56] References Cited
UNITED STATES PATENTS
3,329,709  7/1967  Schmid et al.................. 260/570.6

FOREIGN PATENTS OR APPLICATIONS
85,197  5/1957  Netherlands.................... 260/570.6

*Primary Examiner*—R. V. Hines
*Attorney, Agent, or Firm*—Richard D. Foggio; William H. Edgerton

[57] ABSTRACT

N,N'-Bis[2-(3-substituted-4-hydroxyphenyl)-ethyl or-2-hydroxyethyl]-polymethylenediamines having β-adrenergic stimulant activity particularly as selective bronchodilators, are prepared generally by condensation of an N-benzylphenethylamine with a polymethylene dihalide or by reaction of an α-bromoacetophenone with an N,N'-dibenzyl-polymethylenediamine, with further operations depending on the nature of the 3-substituent, and subsequently hydrogenating catalytically with for example palladium-on-carbon. The key intermediates are also part of the invention.

2 Claims, No Drawings

N,N'-BIS[2-3-SUBSTITUTED-4-HYDROXY-PHEYL)-2-HYDROXYETHYL)]-POLY-METHYLENEDIAMINES

This application is a continuation-in-part of application Ser. No. 148,912 filed June 1, 1971 and now abandoned.

This invention relates to novel N,N'-bis[2-(3-substituted-4-hydroxyphenyl)-ethyl or -2-hydroxyethyl]-polymethylenediamines which have useful pharmacodynamic activity. More specifically the compounds of this invention have utility as β-adrenergic stimulants with relatively greater activity on respiratory smooth muscle than on cardiac muscle. Therefore these compounds have direct bronchodilator action with minimal cardiac stimulation.

Two in vitro pharmacological test procedures used for determining selective β-stimulant activity are: (1) effect on spontaneous tone of guinea pig tracheal chain preparations as a measure of β-stimulant (direct relaxant) effect on airway smooth muscle, and (2) effect on rate of spontaneously beating right atria of the quinea pig as a measure of β-stimulant effect on cardiac muscle. Compounds having selective bronchodilating properties are active in (1) above at a dose lower than is required in (2) above resulting in a positive separation ratio.

The compounds of this invention are represented by the following general structural formula:

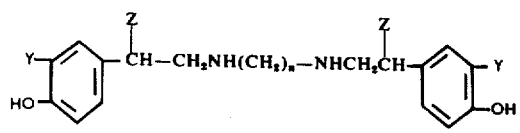

FORMULA I in which:

n represents a positive whole integer of from 4 to 8, preferably 6;

Z represents hydrogen or hydroxy;

Y represents $NH_2$, NHCHO, $NHCOCH_3$, $NHCONH_2$, $NHSO_2R$, $NHCO_2R$, NHCONHR, $NHSO_2NH_2$, $NHSO_2N(CH_3)_2$, $CH_2OH$, $CH_2NH_2$, $CH_2NHSO_2R$, $CH_2NHCONH_2$ or $CH_2SO_2R$; and R represents lower alkyl of from 1 to 5 carbon atoms, straight or branched chain, preferably methyl. In the above formula, each of the Y and Z terms are identical.

The compounds of this invention may be used in the form of a pharmaceutically acceptable acid addition salt having the utility of the free base. Such salts, prepared by methods well known to the art, are formed with both inorganic or organic acids, for example: maleic, fumaric, benzoic, ascorbic, pamoic, succinic, bismethylenesalicylic, methanesulfonic, ethanedisulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

The compounds of formula I above in which Z is hydroxy may be present as diastereoisomers which may be resolved into d, l optical isomers. Resolution of the optical isomers may be conveniently accomplished by fractional crystallization of their salts with optically active acids such as, for example, tartaric, camphor-10-sulfonic, 0,0-di-benzoyltartaric, 0,0-di(p-toluoyl)tartaric, menthyloxyacetic, camphoric, or 2-pyrrolidone-5-carboxylic acids or N-acetyl-tryptophane from appropriate solvents. Unless otherwise specified herein or in the claims, it is intended to include all isomers, whether separated or mixtures thereof.

The compounds of this invention where Z is hydrogen are conveniently prepared from intermediates of the following formula:

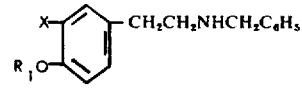

FORMULA II in which X is $NO_2$, $CO_2CH_3$ or $CH_2SO_2R$, R is as defined above and $R_1$ is benzyl or methyl, by reaction with an appropriate polymethylene dihalide, preferably dibromide, in the presence or absence of a solvent with the ratio of phenalkylamine to dihalide at least 2:1. Nonreactive organic solvents which may be used are alcohols such as methanol, ethanol or isopropanol and hydrocarbons such as benzene, toluene or xylene. The reaction is carried out at temperatures from about 20° to 150°C. and for about 2 to 12 hours. The resulting polymethylenediamines of the following formula:

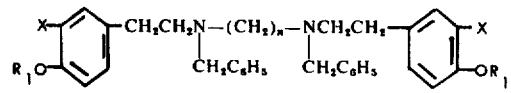

FORMULA III in which X, $R_1$ and n are as defined above, are subjected to further operations to provide the desired benzene ring substituents as set forth in formula I. For example, compounds of formula III wherein X is $NO_2$, $R_1$ is benzyl and n is 4 to 8 are reduced with Raney nickel and hydrazine hydrate or platinum oxide to give the amino compounds of the formula:

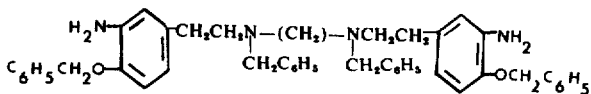

FORMULA IV

These key intermediates are (a) hydrogenated catalytically, preferably with palladium-on-carbon, to give the debenzylated phenethylamines of formula I wherein Y is $NH_2$; (b) treated with acetic anhydride or ethyl formate to give the N-acyl derivatives; (c) reacted with phosgene, then heated to give the isocyanates which are reacted with ammonia or a monosubstituted alkyl amine to yield the ureido derivatives, or reacted with a lower alkanol to yield the carboalkoxyamino derivatives; (d) reacted with an alkyl sulfonyl chloride to give the sulfonamido derivatives; or (e) treated with sulfamyl chloride or N,N-dimethyl sulfamyl chloride to yield the corresponding sulfamoylamino derivatives. The compounds prepared according to the procedures (b) through (e) above are subsequently debenzylated by catalytic hydrogenation, preferably with palladium-on-carbon, to furnish the phenethyl-amines of formula I wherein Y is NHCHO, NHCOCH$_3$, NHCONH$_2$, NHCONHR, NHCO$_2$R, NHSO$_2$R, NHSO$_2$NH$_2$ and NHSO$_2$N(CH$_3$)$_2$, respectively.

Likewise, compounds of formula III above wherein X is CO$_2$CH$_3$, R$_1$ is methyl and n is 4 to 8 are (a) treated with hydrobromic acid to give the corresponding salicylic acid derivatives which are first debenzylated by catalytic hydrogenation, preferably with palladium-on-carbon, and then reduced with for example diborane to yield the phenethylamines of formula I wherein Y is CH$_2$OH; or (b) treated with ammonia to give the corresponding amide derivatives, followed by reduction with for example lithium aluminum hydride to obtain the aminomethyl compounds which in turn are demethylated with for example boron tribromide or sodium ethyl mercaptide and then debenzylated by catalytic hydrogenation, preferably with palladium-on-carbon, to yield the phenethylamines of formula I wherein Y is CH$_2$NH$_2$; or the aminomethyl compounds are first reacted with an alkyl sulfonyl chloride to give the sulfonamidomethyl derivatives or reacted with sodium cyanate in acid to obtain the ureidomethyl compounds, and subsequently demethylated and debenzylated as described above to yield, respectively, the phenethylamines of formula I wherein Y is CH$_2$NHSO$_2$R and CH$_2$NHCONH$_2$.

The compounds of this invention where Z is hydroxy are conveniently prepared from intermediates of the following formula:

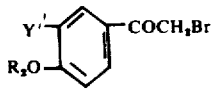

FORMULA V in which Y' is NO$_2$, NHCHO, NHCOCH$_3$, NHCONH$_2$, NHSO$_2$R, NHCO$_2$R, NHCONHR, NHSO$_2$NH$_2$, NHSO$_2$N(CH$_3$)$_2$, CO$_2$CH$_3$, CH$_2$CO$_2$CH$_3$ or CH$_2$SO$_2$R, R is as defined above and R$_2$ is benzyl, acetyl or hydrogen, by reaction with an appropriate N,N'-dibenzyl poly-methylenediamine in equimolar quantities, or with the bromo-ketone being present in excess amount, and in the presence of a nonreactive organic solvent such as acetonitrile at a temperature up to the boiling point of the solvent employed for about 1 to 4 hours. Alternatively the reaction may be carried out in the presence of a condensing agent such as an alkali metal carbonate, for example potassium carbonate. The thus formed polymethylenediamines of the following formula:

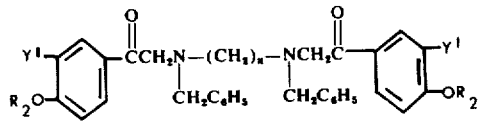

FORMULA VI in which Y', R$_2$ and n are as defined above, are reacted further to furnish the phenethanolamine products of formula I. For example, compounds of formula VI wherein Y' is NO$_2$, R$_2$ is benzyl and n is 4 to 8 are reduced with platinum oxide to give the corresponding aminoalcohols which are then hydrogenated catalytically, preferably with palladium-on-carbon, to yield the debenzylated phenethanolamine products of formula I wherein Y is NH$_2$.

The compounds of formula VI wherein Y' is NHCHO, NHCOCH$_3$, NHCONH$_2$, NHSO$_2$R, NHCO$_2$R, NHCONHR, NHSO$_2$NH$_2$, NHSO$_2$N(CH$_3$)$_2$ or CH$_2$SO$_2$R, R$_2$ is benzyl and n is 4 to 8 are catalytically hydrogenated to reduce the ketone groups and remove the benzyl protective groups, preferably with palladium-on-carbon, or alternatively the ketone groups are first reduced with for example sodium borohydride, followed by debenzylation by similar catalytic hydrogenation, to yield in each instance the phenethanolamine products of formula I wherein Y is NHCHO, NHCOCH$_3$, NHCONH$_2$, NHSO$_2$R, NHCO$_2$R, NHCONHR, NHSO$_2$NH$_2$, NHSO$_2$N(CH$_3$)$_2$ and CH$_2$SO$_2$R.

Compounds of formula VI above wherein Y' is CH$_2$CO$_2$CH$_3$, R$_2$ is acetyl and n is 4 to 8 are treated with a mineral acid such as hydrochloric or hydrobromic acid to give the corresponding 3-hydroxymethyl-4-hydroxy derivatives which are hydrogenated catalytically, preferably with palladium-on-carbon to obtain the phenethanolamine products of formula I wherein Y is CH$_2$OH.

The compounds of formula VI wherein Y' is CO$_2$CH$_3$, R$_2$ is hydrogen and n is 4 to 8 are treated with ammonia to give the amide derivatives of the formula:

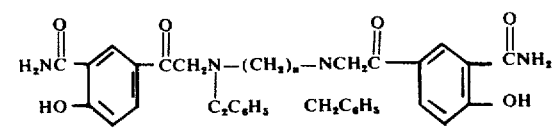

FORMULA VII

These intermediates are (a) reduced with for example lithium aluminum hydride to give the aminomethyl phenethanol derivatives which are then debenzylated by catalytic hydrogenation, preferably with palladium-on-carbon, to yield the phenethanolamine products of formula I wherein Y is CH$_2$NH$_2$; or (b) treated with benzyl chloride to give the benzyloxy protected compounds which are in turn reduced with for example lithium aluminum hydride to obtain the corresponding benzyloxy aminomethyl phenethanol compounds and the latter are reacted with sodium cyanate in acid to yield the ureidomethyl derivatives or reacted with an alkyl sulfonyl chloride to give the sulfonamidomethyl derivatives, subsequently debenzylated by catalytic hydrogenation, preferably with palladium-on-carbon, to furnish the phenethanolamine products of formula I wherein Y is CH$_2$NHCONH$_2$ and CH$_2$NHSO$_2$R, respectively.

The starting materials used herein of formulas II and V are either known or are prepared by methods well-known in the art from readily available materials. Further it will be appreciated that the intermediates described hereinabove, particularly those of formulas III, IV, VI and VII, are valuable intermediates and as such form a part of this invention.

The compounds of this invention may be administered orally or parenterally in conventional dosage unit forms such as tablets, capsules, injectables or the like, by incorporating the appropriate dose of a compound of formula I, with carriers according to accepted pharmaceutical practices. Preferably a compound or an acid addition salt thereof is administered orally to an animal organism in a tablet or capsule comprising an amount sufficient to produce β-adrenergic stimulant activity.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form, or in the form of a troche or lozenge. The amount of solid carrier will vary widely but preferably will be about 25 mg. to about 1 g. If a liquid carrier is used, the preparation will be in the form of a syrup, emulsion, soft gelatin capsule, sterile injectable liquid such as an ampule, or an aqueous or nonaqueous liquid suspension.

Of particular applicability is an aerosol dispensing system wherein the active medicament is incorporated with Freon (fluorohydrocarbon) or other inert propellant in an aerosol container. Such an aerosol system will deliver a metered dose, administered once or twice at a time as needed.

The foregoing is a general description of how to prepare the compounds of this invention. The following examples illustrate the preparation of specific compounds having β-adrenergic stimulant activity. However this should not be construed as a limitation of the invention since appropriate variations in the starting materials will produce other products set forth hereinabove.

EXAMPLE 1

A solution of 17.1 g. (0.1 m.) of benzyl bromide in 100 ml. of dimethylsulfoxide is added slowly to a stirred mixture of 18.2 g. (0.1 m.) of 4-hydroxy-3-nitrophenethylamine in 1 l. of dimethylsulfoxide and 60 ml. of 2N sodium hydroxide at 85°C. After addition is complete the reaction mixture is stirred at 85°C. for an additional two hours, poured into ice-water, saturated with sodium chloride and extracted with ethyl acetate. The organic extract is dried and concentrated to give 4-benzyloxy-3-nitrophenethylamine. The latter (2.72 g., 0.01 m.) in 50 ml. of toluene is rfluxed azeotropically with 1.27 g. (0.012 m.) of benzaldehyde until water formation is completed (about one hour). Solvent is removed by distillation to leave the crude imine. Sodium borohydride (0.38 g., 0.01 m.) is then added to a solution of the above imine in 30 ml. of methanol over a period of 30 minutes and after stirring for an additional hour the reaction mixture is evaporated. The residue is treated with 2N hydrochloric acid and ether. The solid obtained is filtered and washed to give N-benzyl-4-benzyloxy-3-nitrophenethylamine hydrochloride.

A mixture of 145 g. (0.4 m.) of N-benzyl-4-benzyloxy-3-nitrophenethylamine (obtained from the above hydrochloride) and 24.4 g. (0.1 m.) of 1,6-dibromohexane is heated on a steam bath for three hours. The cooled reaction mixture is extracted with water to remove N-benzyl-4-benzyloxy-3-nitro-phenethylamine hydrobromide. The residue is dissolved in 10% aqueous hydrochloric acid and the acid solution is made basic with 40% aqueous sodium hydroxide. This mixture is extracted with ether and the dried ether extract is concentrated in vacuo to leave a residue of N,N'-dibenzyl-N,N'-bis[2-(4-benzyloxy-3-nitrophenyl)-ethyl]-hexamethylenediamine.

A suspension of Raney nickel (approximately 25 g.) in ethanol is added to a solution of 30.3 g. (0.0375 m.) of the above prepared diamine in 500 ml. of ethanol and then 25 ml. of hydrazine hydrate is added dropwise. The resulting mixture is heated at reflux for one hour, filtered and evaporated to dryness. The residue is extracted with ether and the washed and dried extract is acidified with hydrochloric acid to precipitate the tetrahydrochloride salt of N,N'-dibenzyl-N,N'-bis[2-(3-amino-4-benzyloxyphenyl)-ethyl]-hexamethylenediamine.

A solution of 9.7 g. (0.0109 m.) of the above prepared tetrahydrochloride in 65 ml. of methanol and 25 ml. of water is added to a suspension of 1.5 g. of 10% palladium-on-carbon in 10 ml. of water. The mixture is hydrogenated on the Parr apparatus at room temperature using an initial pressure of 60 psi of hydrogen. After four hours the mixture is filtered, an additional 1.5 g. of 10% palladium-on-carbon is added and the hydrogenation is continued. After four hours the reaction mixture is filtered and the filtrate is concentrated in vacuo to give N,N'-bis[2-(3-amino-4-hydroxyphenyl)-ethyl]-hexamethylenediamine tetrahydrochloride.

Similarly, by employing 1,8-dibromooctane in the above condensation with N-benzyl-4-benzyloxy-3-nitrophenethyl-amine as described above there is obtained the corresponding N,N'-dibenzyl-N,N'-bis[2-(4-benzyloxy-3-nitrophenyl)-ethyl]-octamethylenediamine which is carried through the same sequence of reactions, namely reduction with Raney nickel and hydrogenation with palladium-on-carbon, to yield N,N'-bis[2-(3-amino-4-hydroxyphenyl)-ethyl]-octamethylenediamine.

EXAMPLE 2

A mixture of 31.0 g. (0.0415 m.) of N,N'-dibenzyl-N,N'-bis[2-(3-amino-4-benzyloxyphenyl)-ethyl]-hexamethylene-diamine (from the tetrahydrochloride salt prepared as in Example 1) and 50 ml. of acetic anhydride is heated on the steam bath for one hour. The reaction mixture is concentrated in vacuo, the residue is suspended in water and made alkaline with 10% sodium hydroxide. The product is extracted with methylene chloride and the dried extract is concentrated to give N,N'-dibenzyl-N,N'-bis[2-(3-acetamido-4-benzyloxyphenyl)-ethyl]-hexamethylenediamine.

The above prepared compound is treated with ethereal hydrogen chloride to obtain the corresponding dihydrochloride. The latter (6.95 g., 0.0077 m.) with 1.0 g. of 10% palladium-on-carbon in 30 ml. of water and 70 ml. of ethanol is hydrogenated on the Parr apparatus using an initial hydrogen pressure of 60 psi at room temperature. After hydrogen uptake is complete the reaction mixture is filtered and the filtrate concentrated in vacuo to yield N,N'-bis[2-(3-acetamido-4-hydroxyphenyl)-ethyl]-hexamethylenediamine dihydrochloride.

EXAMPLE 3

A mixture of 31.0 g. (0.0415 m.) of N,N'-dibenzyl-N,N'-bis[2-(3-amino-4-benzyloxyphenyl)-ethyl]-hexamethylene-diamine in 230 ml. of ethyl formate is stirred and refluxed for 24 hours. The reaction mixture is evaporated in vacuo and the residue is dissolved in methylene chloride, then washed with dilute hydrochloric acid and saturated sodium chloride solution. The dried solution is evaporated in vacuo to give N,N'-dibenzyl-N,N'-bis[2-(4-benzyloxy-3-formamidophenyl)-ethyl]-hexamethylenediamine.

The thus prepared compound is treated with ethereal hydrogen chloride and the resulting dihydrochloride (2.75 g., 0.00314 m.) is hydrogenated in 70 ml. of ethanol and 30 ml. of water with 1.0 g. of palladium-on-carbon using 60 psi of hydrogen at room temperature. The mixture is filtered and the filtrate evaporated to yield N,N'-bis[2-(3-formamido-4-hydroxyphenyl)-ethyl]-hexamethylenediamine dihydrochloride.

EXAMPLE 4

A stirred solution of 40 g. (0.41 m.) of phosgene in 150 ml. of toluene is held at 25°C. while a mixture of 39.3 g. (0.0525 m.) of N,N'-dibenzyl-N,N'-bis[2-(3-amino-4-benzyloxyphenyl)-ethyl]-hexamethylenediamine and 300 ml. of toluene is added slowly. The resulting mixture is heated to reflux and continued for 30 minutes. Concentration in vacuo gives the bis isocyanate. The latter (40 g.) in 500 ml. of dry benzene is saturated with ammonia. After one hour, the mixture is cooled to give N,N'-dibenzyl-N,N'-bis[2-(4-benzyloxy-3-ureidophenyl)-ethyl]-hexamethylenediamine.

The above prepared compound is treated with ethereal hydrogen chloride to yield the dihydrochloride. A solution of 9.5 g. (0.0109 m.) of the dihydrochloride in 75 ml. of methanol and 25 ml. of water is added to a suspension of 1.5 g. of 10% palladium-on-carbon in 10 ml. of water. The mixture is hydrogenated on the Parr apparatus at room temperature, using an initial pressure of 60 psi of hydrogen. After four hours the mixture is filtered, an additional 1.5 g. of 10% palladium-on-carbon is added and the hydrogenation is continued. After three hours the mixture is filtered and the filtrate is concentrated in vacuo to give N,N'-bis[2-(4-hydroxy-3-ureidophenyl)-ethyl]-hexamethylenediamine dihydrochloride.

Similarly, employing methyl amine, n-butylamine or isopropylamine in the initial reaction with the bis isocyanate and proceeding with the hydrogenation as described above yields the corresponding products, as follows: N,N'-bis[2-(4-hydroxy-3-N'-methylureidophenyl)-ethyl]-hexamethylenediamine, N,N'-bis[2-(3-N'-n-butylureido-4-hydroxyphenyl)-ethyl]-hexamethyl-enediamine and N,N'-bis[2-(4-hydroxy-3-N'-isopropylureidophenyl)-ethyl]-hexamethylenediamine.

EXAMPLE 5

A solution of 12.5 g. of the bis isocyanate prepared from N,N'-dibenzyl-N,N'-bis[2-(3-amino-4-benzyloxyphenyl)-ethyl]-hexamethylenediamine as described in Example 4, in 200 ml. of ethanol is refluxed for two hours. The reaction mixture is concentrated to give N,N'-dibenzyl-N,N'-bis[2-(4-benzyloxy-3-carboethoxyaminophenyl)-ethyl]-hexamethylenediamine.

The dihydrochloride of the above prepared compound (2.2 g., 0.0025 m.), 0.5 g. of 10% palladium-on-carbon and 100 ml. of ethanol is hydrogenated on the Parr apparatus at room temperature, using an initial pressure of 60 psi of hydrogen. When hydrogen uptake is complete the reaction mixture is filtered and the filtrate is concentrated in vacuo to yield N,N'-bis[2-(3-carboethoxyamino-4-hydroxyphenyl)-ethyl]-hexamethylenediamine dihydrochloride.

Similarly, refluxing a solution of the bis isocyanate in methanol or isopropanol and continuing as described above yields as final products N,N'-bis[2-(3-carbomethoxy-amino-4-hydroxyphenyl)-ethyl]-hexamethylenediamine and N,N'-bis[2-(3-carboisopropoxyamino-4-hydroxyphenyl)-ethyl]-hexamethylenediamine, respectively.

EXAMPLE 6

To a solution of 7.5 g. (0.01 m.) of N,N'-dibenzyl-N,N'-bis[2-(3-amino-4-benzyloxyphenyl)-ethyl]-hexamethylene-diamine in 30 ml. of pyridine is added 2.5 g. of methanesulfonyl chloride. The reaction mixture is allowed to stand at room temperature overnight and is then added to excess water to yield N,N'-dibenzyl-N,N'-bis[2-(4-benzyloxy-3-methanesulfonamidophenyl)-ethyl]-hexamethylenediamine.

The dihydrochloride of the above prepared compound is hydrogenated as described in Example 1 to furnish the product N,N'-bis[2-(4-hydroxy-3-methanesulfonamidophenyl)-ethyl]-hexamethylenediamine dihydrochloride.

EXAMPLE 7

To a solution of 36.6 g. (0.049 m.) of N,N'-dibenzyl-N,N'-bis[2-(3-amino-4-benzyloxyphenyl)-ethyl]-hexamethylenediamine in 250 ml. of dry pyridine is added 28.6 g. (0.2 m.) of dimethylsulfamoyl chloride in 40 ml. of pyridine at 0°-10°C. The reaction mixture is stirred in the cold overnight, then poured into water and extracted with ether. The ether extract is washed with water and extracted with dilute aqueous potassium hydroxide. The latter extract is washed with ether, acidified with hydrochloric acid and extracted with methylene chloride. The dried extract is evaporated in vacuo to give N,N'-dibenzyl-N,N'-bis[2-(4-benzyloxy-3-N,N-dimethylsulfamoylaminophenyl)-ethyl]-hexamethylenediamine.

The dihydrochloride of the thus prepared compound (9.26 g., 0.01 m.) is hydrogenated in 30 ml. of water and 70 ml. of ethanol with 0.5 g. of palladium-on-carbon at room temperature for two hours in the Parr apparatus. The reaction mixture is filtered, an additional 1 g. of palladium-on-carbon is added and the hydrogenation is continued for two hours. The mixture is filtered and the filtrate evaporated to yield N,N'-bis[2-(3-N,N-dimethylsulfamoylamino-4-hydroxyphenyl)-ethyl]-hexamethylenediamine dihydrochloride.

EXAMPLE 8

To a stirred solution of 5.8 g. (0.05 m.) of sulfamyl chloride in 75 ml. of dry benzene at 10°C. is added, in small portions, 37.4 g. (0.05 m.) of N,N'-dibenzyl-N,N'-bis[2-(3-amino-4-benzyloxyphenyl)-ethyl]-hexamethylenediamine. After the mixture is stirred at 10°-20°C. for 30 minutes, it is extracted with 5% aqueous sodium hydroxide. Adding dilute hydrochloric acid to the basic extract precipitates the product, N,N'-dibenzyl-N,N'-bis[2-(4-benzyloxy-3-sulfamoylaminophenyl)-ethyl]-hexamethylenediamine.

Proceeding as described in Example 7, namely hydrogenation of the corresponding dihydrochloride yields N,N'-bis[2-(4-hydroxy-3-sulfamoylaminophenyl)-ethyl]-hexamethylenediamine dihydrochloride.

EXAMPLE 9

A solution of 2.44 g. (0.01 m.) of 3-carbomethoxy-4-methoxyphenethylamine (prepared from 3-carbomethoxy-4-methoxybenzyl chloride by reaction with sodium cyanide followed by catalytic reduction of the resulting benzyl nitrile) in 25 ml. of toluene is refluxed azeotropically with 1.27 g. (0.012 m.) of benzaldehyde for one hour, then the solution is concentrated to give the N-benzal derivative. Sodium borohydride (0.38 g., 0.01 m.) is then added to a solution of the N-benzal derivative in 25 ml. of methanol over a period of 30 minutes. After being stirred for an additional hour at 25°C. the reaction mixture is evaporated. The residue is treated with 2N hydrochloric acid and ether to precipitate N-benzyl-3-carbomethoxy-4-methoxyphenethylamine hydrochloride.

A mixture of 119.5 g. (0.4 m.) of N-benzyl-3-carbomethoxy-4-methoxyphenethylamine (obtained from the above hydrochloride) and 24.4 g. (0.1 m.) of 1,6-dibromohexane in 250 ml. of acetonitrile is refluxed for three hours. The cooled reaction mixture is diluted with ether to precipitate N-benzyl-3-carbomethoxy-4-methoxyphenethylamine hydrobromide. The mixture is filtered and the filtrate is concentrated in vacuo to leave a residue of N,N'-dibenzyl-N,N'-bis[2-(3-carbomethoxy-4-methoxyphenyl)-ethyl]-hexamethylenediamine.

A solution of 3.1 g. (0.0041 m.) of the dihydrochloride of the above prepared diamine in 30 ml. of methanol and 25 ml. of an aqueous solution of ammonia (d. 0.880) is allowed to stand at room temperature about 20 hours. The mixture is evaporated under reduced pressure to give a residue which with methanolic hydrochloric acid yields the dihydrochloride of N,N'-dibenzyl-N,N'-bis[2-(3-carboxamido-4-methoxyphenyl)-ethyl]-hexamethylenediamine.

A solution of the above carboxamido free base liberated by aqueous ammonia from 3.61 g. (0.005 m.) of the dihydrochloride is added to a warm, stirred suspension of 1.5 g. of lithium aluminum hydride in 20 ml. of tetrahydrofuran. After stirring at reflux for about 17 hours the cooled reaction mixture is treated with 5 ml. of water, filtered and the filtrate is evaporated. The residue is dissolved in ethanol and ethereal hydrogen chloride is added to precipitate the tetrahydrochloride of N,N'-dibenzyl-N,N'-bis[2-(3-aminomethyl-4-methoxyphenyl)-ethyl]-hexamethylenediamine.

To a suspension of 12 g. (0.0177 m.) of the free base derived from the above tetrahydrochloride in 75 ml. of methylene chloride is added gradually 9.0 ml. of boron tribromide, with stirring in an ice bath. The ice bath is removed and the mixture is stirred for one hour. The reaction mixture is evaporated in vacuo, excess methanol is added gradually and the solution evaporated. The residue is dissolved in water and the solution is neutralized with sodium bicarbonate to give N,N'-dibenzyl-N,N'-bis[2-(3-aminomethyl-4-hydroxyphenyl)-ethyl]-hexamethylenediamine.

A solution of 17.3 g. (0.0218 m.) of the tetrahydrochloride prepared from the above free base in 75 ml. of methanol and 25 ml. of water is hydrogenated with palladium-on-carbon as described in Example 1 to give N,N'-bis[2-(3-aminomethyl-4-hydroxyphenyl)-ethyl]-hexamethylenediamine tetrahydrochloride.

EXAMPLE 10

Following the procedure of Example 6, 2.5 g. of methanesulfonyl chloride is added to a solution of 6.78 g. (0.01 m.) of N,N'-dibenzyl-N,N'-bis[2-(3-aminomethyl-4-methoxyphenyl)-ethyl]-hexamethylenediamine in 30 ml. of pyridine and the mixture is allowed to stand at room temperature overnight to yield N,N'-dibenzyl-N,N'-bis[2-(3-methanesulfonamidomethyl-4-methoxyphenyl)-ethyl]-hexamethylenediamine. The latter as the dihydrochloride is demethylated and then debenzylated as described in Example 9 to furnish the product N,N'-[2-(4-hydroxy-3-methanesulfonamidomethylphenyl)-ethyl]-hexamethylenediamine dihydrochloride.

EXAMPLE 11

A solution of 54.2 g. (0.08 m.) of N,N'-dibenzyl-N,N'-bis[2-(3-aminomethyl-4-methoxyphenyl)-ethyl]-hexamethylenediamine in 500 ml. of acetic acid and 175 ml. of water is stirred at 40°C. while a slurry of 23.5 g. of 90% sodium cyanate (21.2 g., 0.32 m.) in 160 ml. of water is added in portions. The resulting mixture is stirred at 40°C. for one hour, diluted with 1600 ml. of water and extracted with methylene chloride. The extract is washed with sodium carbonate, dried and evaporated in vacuo to give N,N'-dibenzyl-N,N'-bis[2-(4-methoxy-3-ureidomethylphenyl)-ethyl]-hexamethylenediamine. The latter as the dihydrochloride is demethylated and debenzylated as described in Example 9 to give N,N'-bis[2-(4-hydroxy-3-ureidomethylphenyl)-ethyl]-hexamethylenediamine dihydrochloride.

EXAMPLE 12

A mixture of 1.56 g. (0.0023 m.) of N,N'-dibenzyl-N,N'-bis[2-(3-carbomethoxy-4-methoxyphenyl)-ethyl]-hexamethylenediamine and 40 ml. of 48% aqueous hydrobromic acid is refluxed for four hours. The cooled reaction mixture is filtered to give N,N'-dibenzyl-N,N'-bis[2-(3-carboxy-4-hydroxyphenyl)-ethyl]-hexamethylenediamine dihydrobromide. The latter is hydrogenated with palladium-on-carbon as described in Example 1 to yield N,N'-bis[2-(3-carboxy-4-hydroxyphenyl)-ethyl]-hexamethylenediamine dihydrobromide. The free base obtained from this dihydrobromide (0.8 g., 0.0018 m.) is added to an ice cold solution of 40 ml. of 1M borane in tetrahydrofuran (0.04 m.) while stirring under nitrogen. The temperature is maintained at 0°C. for 20 hours, the solution is then refluxed for one hour and concentrated in vacuo. Several portions of methanol are added, the solution is concentrated and the residue is dissolved in ethanol and filtered. Sulfuric acid is added to pH 2.0 to give N,N'-bis[2-(4-hydroxy-3-hydroxymethylphenyl)-ethyl]-hexamethylenediamine sulfate.

EXAMPLE 13

To a stirred solution of 5.42 g. (0.02 m.) of 4-benzyloxy-3-nitroacetophenone in 100 ml. of chloroform is added 3.2 g. (0.02 m.) of bromine. The mixture is stirred at room temperature for about 45 minutes and the solution is concentrated in vacuo at 25°–30°C. to leave 4-benzyloxy-α-bromo-3-nitroacetophenone. The latter (35.0 g., 0.1 m.) in 250 ml. of acetonitrile is stirred at 25°C. with 29.6 g. (0.1 m.) of N,N'-dibenzylhexamethylenediamine for two hours. The cooled reaction mixture is filtered to remove the dihydrobromide of N,N'-dibenzyl-hexamethylenediamine. Acidification of the filtrate with ethereal hydrogen chloride gives N,N'-dibenzyl-N,N'-bis[2-(4-benzyloxy-3-nitrophenyl)-2-oxoethyl]-hexamethylenediamine dihydrochloride.

The above prepared dihydrochloride is hydrogenated in methanol solution with platinum oxide catalyst to obtain the dihydrochloride of N,N'-dibenzyl-N,N'-bis[2-(3-amino-4-benzyloxyphenyl)-2-hydroxyethyl]-hexamethylenediamine. The latter is debenzylated as described in Example 1 with palladium-on-carbon and a methanolic solution of the product is treated with ethereal hydrogen chloride to yield N,N'-bis[2-(3-amino-4-hydroxyphenyl)-2-hydroxyethyl]-hexamethylenediamine tetrahydrochloride, m.p. 202°–205°C.

EXAMPLE 14

A mixture of 20.0 g. (0.083 m.) of 3-amino-4-benzyloxyacetophenone and 50 ml. of acetic anhydride is heated on the steam bath for one hour. The resulting solution is concentrated in vacuo, the residual solid is suspended in water and the mixture made alkaline with 10% sodium hydroxide. The crystalline product is extracted with methylene chloride, and the dried extract is concentrated to give 3-acetamido-4-benzyloxyacetophenone, m.p. 132°–134°C.

To a stirred solution of 8.6 g. (0.03 m.) of 3-acetamido-4-benzyloxyacetophenone and 2.6 g. (0.03 m.) of 2-pyrrolidone in 300 ml. of tetrahydrofuran is added dropwise a solution of 15.0 g. (0.03 m.) of pyrrolidone hydrotribromide in 300 ml. of tetrahydrofuran. The mixture is stirred at room temperature for 18 hours, filtered and the filtrate concentrated in vacuo to yield 3-acetamido-4-benzyloxy-α-bromoacetophenone, m.p. 163°–166°C.

A mixture of 3.48 g. (0.01 m.) of 3-acetamido-4-benzyloxy-α-bromoacetophenone and 2.96 g. (0.01 m.) of N,N'-dibenzyl-hexamethylenediamine in 50 ml. of acetonitrile is stirred at 25°C. for two hours. The cooled reaction mixture is filtered and the filtrate acidified with ethereal hydrogen chloride to give N,N'-dibenzyl-N,N'-bis[2-(3-acetamido-4-benzyloxyphenyl)-2-oxoethyl]-hexamethylenediamine dihydrochloride. The latter is hydrogenated with 10% palladium-on-carbon to yield N,N'-bis[2-(3-acetamido-4-hydroxyphenyl)-2-hydroxyethyl]-hexamethylenediamine dihydrochloride, m.p. 218°–219°C.d.

Similarly, equimolar amounts of 3-acetamido-4-benzyloxy-α-bromoacetophenone and N,N'-dibenzyl-tetramethylene-diamine are condensed as described above to give the N,N'-dibenzyl-N,N'-bis[2-(3-acetamido-4-benzyloxyphenyl)-2-oxoethyl]-tetramethylenediamine which is likewise hydrogenated to furnish N,N'-bis[2-(3-acetamido-4-hydroxyphenyl)-2-hydroxyethyl]-tetramethylenediamine.

EXAMPLE 15

A solution of 20 g. (0.083 m.) of 3-amino-4-benzyloxyacetophenone in 230 ml. of ethyl formate is stirred and refluxed for 24 hours. The reaction mixture is evaporated in vacuo and the residue is dissolved in methylene chloride, then washed with dilute hydrochloric acid and saturated sodium chloride solution. The dried solution is evaporated in vacuo to give a residue which upon trituration with ether gives 4-benzyloxy-3-formamidoacetophenone, m.p. 121°–123°C.

To a solution of 17.5 g. (0.0648 m.) of 4-benzyloxy-3-formamidoacetophenone and 5.51 g. (0.0648 m.) of 2-pyrrolidone in 650 ml. of tetrahydrofuran, stirred at room temperature, is added dropwise a solution of 32.2 g. (0.0648 m.) of pyrrolidone hydrotribromide in 650 ml. of tetrahydrofuran. The mixture is stirred overnight at room temperature, filtered and the filtrate evaporated. The residue is dissolved in methylene chloride, washed with water, dried and evaporated to leave 4-benzyloxy-α-bromo-3-formamidoacetophenone, m.p. 124°–128°C.

Following the procedures of Example 14, equimolar amounts of 4-benzyloxy-α-bromo-3-formamidoacetophenone and N,N'-dibenzyl-hexamethylenediamine are stirred in acetonitrile at 25°C. for two hours to give N,N'-dibenzyl-N,N'-bis[2-(4-benzyloxy-3-formamidophenyl)-2-oxoethyl]-hexamethylenediamine which is similarly hydrogenated to furnish N,N'-bis[2-(3-formamido-4-hydroxyphenyl)-2-hydroxyethyl]-hexamethylenediamine.

EXAMPLE 16

A stirred solution of 40 g. (0.41 m.) of phosgene in 150 ml. of toluene is held at 25°C. with a cooling bath while a mixture of 25.2 g. (0.105 m.) of 3-amino-4-benzyloxy-acetophenone and 220 ml. of toluene are added slowly. The mixture is heated to reflux and continued for 30 minutes. Nitrogen is passed through the mixture and then concentrated in vacuo to give a crystalline isocyanate, m.p. 105°–106°C.

A stirred solution of the isocyanate (28.0 g.) in 500 ml. of dry benzene is saturated with ammonia. After one hour, the mixture is cooled to give the crystalline 4-benzyloxy-3-ureidoacetophenone, m.p. 184°–186°C.

To a stirred solution of 5.7 g. (0.02 m.) of 4-benzyloxy-3-ureidoacetophenone in 100 ml. of chloroform is added 3.2 g. (0.02 m.) of bromine. The mixture is stirred at room temperature for about 45 minutes and the solution is concentrated in vacuo at 25°–30°C. to give 4-benzyloxy-α-bromo-3-ureidoacetophenone.

Following the procedures of Example 14, the above prepared acetophenone and N,N'-dibenzyl-hexamethylenediamine are refluxed in acetone for 12 hours and the resulting N,N'-dibenzyl-N,N'-bis[2-(4-benzyloxy-3-ureidophenyl)-2-oxoethyl]-hexamethylenediamine is hydrogenated to yield N,N'-bis[2-(4-hydroxy-3-ureidophenyl)-2-hydroxyethyl]-hexamethylenediamine.

Similarly, 4-benzyloxy-α-bromo-3-(N'-methylureido)-acetophenone, prepared from the above isocyanate by reacting with methyl amine followed by bromination as described above, is refluxed in acetone for 12 hours with N,N'-dibenzyl-hexamethylenediamine to give the corresponding N,N'-dibenzyl-N,N'-bis[2-(4-benzyloxy-3-N'-methylureidophenyl)-2-oxoethyl]-hexamethylenediamine which in turn is hydrogenated with palladium-on-carbon to furnish the product N,N'-bis[2-(4-hydroxy-3-N'-methylureidophenyl)-2-hydroxyethyl]-hexamethylenediamine.

EXAMPLE 17

A solution of the isocyanate (12.5 g.), prepared as in Example 16, in 170 ml. of ethanol is refluxed for two hours. The reaction mixture is concentrated and the residue is triturated with hexane to give the crystalline 4-benzyloxy-3-carboethoxyaminoacetophenone, m.p. 84°–86°C.

To a stirred solution of 1.6 g. (0.005 m.) of 4-benzyloxy-3-carboethoxyaminoacetophenone in 20 ml. of chloroform and 0.2 g. of benzoyl peroxide is added 0.84 g. (5% excess) of bromine in 2 ml. of chloroform. The mixture is stirred at room temperature for about 45 minutes in the presence of a spotlight and the solution is concentrated in vacuo at 35°–45°C. to give 4-benzyloxy-α-bromo-3-carboethoxyaminoacetophenone, m.p. 98°–100°C.

By employing the procedures described in Example 14 the above prepared bromoketone and N,N'-dibenzyl-hexamethylenediamine are stirred at 25°C. in acetone for two hours to yield N,N'-dibenzyl-N,N'-bis[2-(4-benzyloxy-3-carboethoxyaminophenyl)-2-oxoethyl]-hexamethylenediamine which in turn is similarly hydrogenated to give N,N'-bis[2-(3-carboethoxyamino-4-hydroxyphenyl)-2-hydroxyethyl]-hexamethylenediamine; m.p. dihydrochloride 227°–228°C.d.

EXAMPLE 18

A mixture of 3.98 g. (0.01 m.) of 4-benzyloxy-3-methanesulfonamido-α-bromoacetophenone (U.S. Pat. No. 3,478,149) and 2.96 g. (0.01 m.) of N,N'-dibenzyl-hexamethylenediamine in 50 ml. of acetonitrile is stirred at 25°C. for two hours. The cooled reaction mixture is filtered and the filtrate is acidified with ethereal hydrogen chloride to give N,N'-dibenzyl-N,N'-bis[2-(4-benzyloxy-3-methanesulfonamidophenyl)-2-oxoethyl]-hexamethylenediamine dihydrochloride. The latter is hydrogenated with 10% palladium-on-carbon to yield N,N'-bis[2-(4-hydroxy-3-methanesulfonamidophenyl)-2-hydroxyethyl]-hexamethylenediamine dihydrochloride, m.p. 194°–195°C.

EXAMPLE 19

A solution of 23.6 g. (m.) of 3-amino-4-benzyloxyacetophenone in 200 ml. of dry pyridine is treated with 28.6 g. (0.2 m.) of dimethylsulfamoyl chloride in 40 ml. of pyridine at 0°–10°C. The reaction mixture is stirred in the cold overnight, then poured into water and extracted with ether. The ether extract is washed with water and extracted with dilute aqueous potassium hydroxide. The latter extract is washed with ether, acidified with hydrochloric acid and extracted with methylene chloride. The dried methylene chloride solution is evaporated in vacuo to give 4-benzyloxy-3-(N,N-dimethylsulfamoylamino)-acetophenone, m.p. 108°–109.5°C.

To a stirred solution of 1.74 g. (0.005 m.) of 4-benzyloxy-3-(N,N-dimethylsulfamoylamino)-acetophenone in 25 ml. of chloroform is added a solution of 0.9 g. (0.0056 m.) of bromine in 25 ml. of chloroform. The mixture is stirred at room temperature for about 30 minutes and the solution is concentrated to leave 4-benzyloxy-α-bromo-3-(N,N-dimethylsulfamoylamino)-acetophenone, m.p. 80°–85°C.

Following the procedures of Example 14, the above prepared acetophenone is reacted with N,N'-dibenzyl-hexamethylenediamine in acetonitrile at 25°C. to give N,N'-dibenzyl-N,N'-bis[2-(4-benzyloxy-3-N,N-dimethylsulfamoylaminophenyl)-2-oxoethyl]-hexamethylenediamine which is similarly hydrogenated to yield N,N'-bis[2-(3-N,N-dimethylsulfamoylamino-4-hydroxy-phenyl)-2-hydroxyethyl]-hexamethylenediamine.

Similarly, 4-benzyloxy-α-bromo-3-sulfamoylaminoacetophenone, prepared from 3-amino-4-benzyloxyacetophenone by reacting with sulfamyl chloride in dry benzene at 10°–20°C. followed by bromination as described above, is refluxed in acetone for 12 hours with N,N'-dibenzyl-hexamethylenediamine to give N,N'-dibenzyl-N,N'-bis[2(4-benzyloxy-3-sulfamoylaminophenyl)-2-oxoethyl]-hexamethylenediamine which is then hydrogenated with palladium-on-carbon to yield N,N'-bis[2-(4-hydroxy-3-sulfamoylaminophenyl)-2-hydroxyethyl]-hexamethylenediamine.

EXAMPLE 20

A mixture of 3.29 g. (0.01 m.) of 4-acetoxy-3-acetoxymethyl-α-bromoacetophenone (South African Pat. No. 67/5591) and 2.96 g. (0.01 m.) of N,N'-dibenzyl-hexamethylenediamine in 50 ml. of acetonitrile is stirred at 25°C. for two hours. The cooled reaction mixture is filtered, the filtrate is acidified with concentrated hydrochloric acid and the solution is allowed to stand for 18 hours to precipitate N,N'-dibenzyl-N,N'-bis[2-(4-hydroxy-3-hydroxymethylphenyl)-2-oxoethyl]-hexamethylenediamine dihydrochloride. The latter is hydrogenated with 10% palladium-on-carbon to yield N,N'-bis[2-(4-hydroxy-3-hydroxymethylphenyl)-2-hydroxyethyl]-hexamethylenediamine dihydrochloride, m.p. 155°–160°C.D.

EXAMPLE 21

A mixture of 2.73 g. (0.01 m.) of 3-carbomethoxy-4-hydroxy-α-bromoacetophenone (South African Pat. No. 67/5591) and 2.96 g. (0.01 m.) of N,N'-dibenzyl-hexamethylenediamine in 50 ml. of acetonitrile is stirred at 25°C. for two hours. The cooled reaction mixture is filtered and the filtrate is acidified with ethereal hydrogen chloride to give N,N'-dibenzyl-N,N'-bis[2-(3-carbomethoxy-4-hydroxyphenyl)-2-oxoethyl]-hexamethylenediamine dihydrochloride.

A solution of 15 g. (0.02 m.) of the above prepared dihydrochloride in 125 ml. of methanol and 125 ml. of aqueous ammonia (d. 0.880) is allowed to stand in a stoppered flask for six days. The mixture is then evaporated to dryness and the residue is extracted with ether. Treatment of the ethereal mixture with hydrogen chloride gives N,N'-dibenzyl-N,N'-bis[2-(3-carboxamido-4-hydroxyphenyl)-2-oxoethyl]-hexamethylenediamine dihydrochloride.

Following the procedure outlined in Example 9, a solution of the above carboxamido free base liberated by aqueous ammonia from 0.0025 m. of the dihydrochloride is added to a suspension of 1.5 g. of lithium aluminum hydride to yield after treating the product with ethereal hydrogen chloride the tetrahydrochloride of N,N'-dibenzyl-N,N'-bis[2-(3-aminomethyl-4-hydroxyphenyl)-2-hydroxyethyl]-hexamethylenediamine. Hydrogenation with palladium-on-carbon gives N,N'-bis[2-(3-aminomethyl-4-hydroxyphenyl)-2-hydroxyethyl]-hexamethylenediamine tetrahydrochloride.

EXAMPLE 22

A mixture of 28.7 g. of N,N'-dibenzyl-N,N'-bis[2-(3-carboxamido-4-hydroxyphenyl)-2-oxoethyl]-hexamethylenediamine (obtained from the dihydrochloride as prepared in Example 21), 12.0 g. of potassium carbonate, 3.0 g. of sodium iodide and 9.1 ml. of benzyl chloride in 50 ml. of methyl-ethylketone is heated at reflux for four hours. The cooled reaction mixture is filtered and the filtrate is evaporated to dryness to leave N,N'-dibenzyl-N,N'-bis[2-(4-benzyloxy-3-carboxamidophenyl)-2-oxoethyl]-hexamethylenediamine.

A mixture of 15 g. (0.0175 m.) of the above carboxamido compound and 6 g. of lithium aluminum hydride in 400 ml. of tetrahydrofuran is heated at reflux for 22 hours. After water is added, the reaction mixture is evaporated to dryness and the residue is partitioned between ether and water. The ether extract is treated with hydrogen chloride to give the tetrahydrochloride of N,N'-dibenzyl-N,N'-bis[2-(3-aminomethyl-4-benzyloxyphenyl)-2-hydroxyethyl]-hexamethylenediamine.

A solution of 3.9 g. (0.004 m.) of the above tetrahydrochloride in 50 ml. of ethanol containing 2.3 g. of potassium cyanate is heated for two hours. The reaction mixture is evaporated to dryness and the residue is partitioned between ether and aqueous sodium carbonate. The ether extract is washed with water, dried and evaporated to yield N,N'-dibenzyl]-N,N'-bis[2-(4-benzyloxy-3-ureidomethylphenyl)-2-hydroxyethyl]-hexamethylenediamine. The latter, as the dihydrochloride, is hydrogenated with 10% palladium-on-carbon to give N,N'-bis [2-(4-hydroxy-3-ureidomethylphenyl)-2-hydroxyethyl]-hexamethylenediamine dihydrochloride.

EXAMPLE 23

To a solution of 9.35 g. of N,N'-dibenzyl-N,N'-bis[2-(3-aminomethyl-4-benzyloxyphenyl)-2-hydroxyethyl]-hexamethylenediamine in 50 ml. of pyridine is added 2.5 ml. of methanesulfonyl chloride at room temperature. After 18 hours the reaction mixture is added to an excess of 2N hydrochloric acid and extracted with chloroform. The extract is neutralized with sodium bicarbonate, washed, dried and evaporated to give N,N'-dibenzyl-N,N'-bis[2-(4-benzyloxy-3-methanesulfonamido-methylphenyl)-2-hydroxyethyl]-hexamethylenediamine. The latter, as the dihydrochloride, is hydrogenated with palladium-on-carbon to yield N,N'-bis[2-(4-hydroxy-3-methanesulfonamido-methylphenyl)-2-hydroxyethyl]-hexamethylenediamine dihydrochloride.

EXAMPLE 24

To a mixture of 260 cc. of 37% formaldehyde and 1800 cc. of concentrated hydrochloric acid is added 400 g. of p-hydroxyacetophenone at a temperature of about 45°C. The mixture is maintained at 50°C. for two hours, filtered, and washed with water to give 3-chloromethyl-4-hydroxyacetophenone, m.p. 154°C. dec.

A mixture of 40 g. of 3-chloromethyl-4-hydroxyacetophenone and 26 g. of magnesium methyl sulfinate in 500 ml. of ethanol is refluxed with stirring for 3 hours. The reaction mixture is then concentrated in vacuo. The resultant oil is redissolved in chloroform and washed with water. The chloroform is dried and evaporated to give 4-hydroxy-3-methyl-sulfonylmethylacetophenone, m.p. 206.5°-208.5°C.

A mixture of 14.0 g. of 4-hydroxy-3-methylsulfonylmethylacetophenone, 9.3 g. of potassium carbonate, 7.8 ml. of benzyl chloride and a catalytic amount of sodium iodide in 250 ml. of acetone and 250 ml. of water is refluxed with stirring for 16 hours. The acetone is removed and the aqueous phase is extracted with chloroform, washed with water, dried and evaporated to yield an oil which is recrystallized in isopropyl alcohol to give crystalline 4-benzyloxy-3-methyl-sulfonyl-methylacetophenone, m.p. 94°-97°C.

To a stirred solution of 7.7 g. of 4-benzyloxy-3-methylsulfonylmethylacetophenone and 2.15 g. of 2-pyrrolidone in 300 ml. of tetrahydrofuran is added 12.5 g. of pyrrolidone hydrotribromide (PHT) and the stirring is continued for 56 hours at room temperature. The mixture is filtered and the filtrate concentrated in vacuo to give an oil which crystallizes upon standing. The crystals are redissolved in chloroform. The chloroform solution is washed with water, dried and concentrated to yield a solid which is recrystallized from acetonitrile to give 4-benzyloxy-α-bromo-3-methylsulfonylmethylacetophenone, m.p. 143°-144°C.

Following the procedures of Example 14, equimolar amounts of 4-benzyloxy-α-bromo-3-methylsulfonylmethylacetophenone and N,N'-dibenzyl-hexamethylenediamine are stirred in acetonitrile at 25°C. for two hours to give N,N'-dibenzyl-N,N'-bis[2-(4-benzyloxy-3-methylsulfonylmethylphenyl)-2-oxoethyl]-hexamethylenediamine which is similarly hydrogenated to furnish N,N'-bis[2-(4-hydroxy-3-methylsulfonylmethylphenyl)-2-hydroxyethyl]-hexamethylenediamine; m.p. dihydrochloride 177°-179°C.

EXAMPLE 25

A solution of 10.0 g. (0.0252 m.) of 4-benzyloxy-α-bromo-3-methylsulfonylmethylacetophenone in 50 ml. of dimethyl-sulfoxide is allowed to stand for 40 hours and then is poured into water. The mixture is extracted with chloroform and the extract is washed with water, dried and evaporated to give 4-benzyloxy-3-methylsulfonylmethylphenyl glyoxal, m.p. 108°-110°C.

To a warm slurry of 3.32 g. (0.01 m.) of the above prepared phenyl glyoxal in 40 ml. of methanol is added a solution of 0.58 g. (0.005 m.) of 1,6-diaminohexane in methanol. After warming for 20 minutes the reaction mixture is filtered to give N,N'-bis[2-(4-benzyloxy-3-methylsulfonylmethylphenyl)-2-oxoethylidene]-hexamethylenediamine, m.p. 162°-163°C.

The above diamine is slurried in absolute ethanol and 1.0 g. of sodium borohydride is added. The mixture is refluxed for two hours and filtered hot to yield N,N'-bis[2-(4-benzyloxy-3-methylsulfonylmethylphenyl)-2-hydroxyethyl]-hexamethylenediamine, m.p. 146°-148.5°C.

This bis aminoalcohol (2.0 g., 0.0027 m.) is hydrogenated as a slurry in methanol on a Parr shaker over 1.0 g. of palladium-on-carbon for about five hours. The reaction mixture is filtered, evaporated and the residue in methanol is treated with ethereal-hydrogen chloride to give N,N'-bis[2-(4-hydroxy-3-methylsulfonylmethylphenyl)-2-hydroxyethyl]-hexamethylenediamine dihydrochloride, m.p. 177°-179°C.

What is claimed is:

1. A chemical compound of the formula:

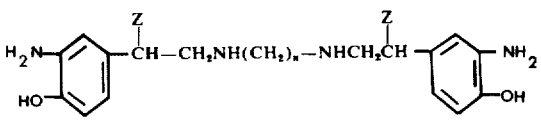

or a pharmaceutically acceptable acid addition salt of said compound, wherein:

$n$ is a positive whole integer from 4 to 8; and
Z is hydroxy.

2. A chemical compound according to claim 1 in which $n$ is 6.

* * * * *